United States Patent [19]
Goldman et al.

[11] Patent Number: 5,189,018
[45] Date of Patent: Feb. 23, 1993

[54] METHOD FOR REDUCTION OF CENTRAL NERVOUS SYSTEM (CNS) EDEMA RESULTING FROM HEAD AND SPINAL CORD TRAUMA

[75] Inventors: Harold Goldman, Southfield; Sharon Murphy, Sterling Heights; Marilyn Morehead, Detroit, all of Mich.

[73] Assignee: Wayne State University, Detroit, Mich.

[21] Appl. No.: 747,794

[22] Filed: Aug. 19, 1991

[51] Int. Cl.$^5$ .............................................. A61K 37/00
[52] U.S. Cl. ......................................... 514/10; 514/17
[58] Field of Search ..................................... 514/10, 17

Primary Examiner—S. J. Friedman
Attorney, Agent, or Firm—Reising, Ethington, Barnard, Perry & Milton

[57] ABSTRACT

A method for reducing the rise in intracranial pressure accompanying head trauma includes the steps of significantly reducing the mean trauma induced increase in blood brain barrier permeability by administering an effective dose of an analog of amino acids 4–9 of adrenocorticotropin hormone, thereby significantly reducing the peak rise in intracranial pressure which normally acompanies the trauma.

9 Claims, 9 Drawing Sheets

METHOD FOR REDUCTION OF CENTRAL NERVOUS SYSTEM (CNS) EDEMA RESULTING FROM HEAD AND SPINAL CORD TRAUMA

TECHNICAL FIELD

The present invention relates to a novel method of treating head trauma and reducing the rise in intracranial pressure accompanying head trauma. More specifically, the present invention provides a novel use of adrenocorticotropin hormone analogs for treating the serious effects caused by head trauma.

BACKGROUND OF THE INVENTION

Head injury kills more persons under the age of 44 than all other diseases combined and accounts for 500,000 hospitalizations each year in which 70,000 are severe cases and some 2000 persons are left in a persistent vegetative state. These injures cost over a billion dollars for hospitalized patients alone. Moreover, some 165,000 children will be hospitalized, 16,000 of which have moderate to severe symptoms. It can be concluded that head injuries are a very serious health problem in the United States alone.

In both humans and in animal models, the sequence of events following head trauma, referred to as post-concussion syndrome can be divided into two phases (1). The first phase is an acute phase consisting of the first six hours during which the organism may be lethargic but functional. During this phase, intracranial pressure is less than 15 mmHg. A second phase begins at six hours and extends for up to five days during which the organism may become comatose. In this second phase, intracranial pressure increases to more than 20 mmHg at 24 hours and it may approach 40 mmHg in an animal model of closed head injury. During this second phase, sometimes referred to as the secondary injury, very serious irreversible brain damage can occur which has to date proven to be intractable to treatment in clinical settings.

Treatments currently used for the above discussed injuries all have serious limitations and are potentially debilitating because of the side effects resulting from the administration thereof. The most important requirement of these treatments is to reduce the rising intracranial pressure as soon as possible. Currently, therapy consists of intravenous infusion of hypertonic mannitol solution. The hypertonic solution was originally believed to act by causing an increase in the osmotic gradient between blood and brain thus drawing water from the edematous brain so as to reduce the dangerously high intracranial pressure (2).

Mannitol may also function by reducing ventricular cerebral spinal fluid. Very recently, it has been shown that mannitol is a free-radical scavenger and may be effective in this mode against rising intracranial pressure by reducing inflammatory oxygen free-radicals, a proposed mechanism for the increased brain water content (4). A problem exists with the use of mannitol in such treatments because such treatment can lead to fluid and electrolyte disturbances. If serum osmolality increases above 320 mosmol/liter, renal failure can result.

Other treatments that have been used in the past consist of unreliable barbiturate therapy which additionally has the potential for causing arterial hypotension, and corticosteroid therapy which has proven to be ineffective in reducing the high intracranial pressure resulting from moderate concussion. Neither of the aforementioned treatments is able to reliably improve the outcome (2).

It can be concluded that despite recent technological developments that enable physicians to closely monitor head injured patients, treatment of the most serious complication of head injury which is the edematous brain still relies on clinically questionable methods. Such methods are now more than 30 years old and still have significant limitations and toxicities.

Human adrenocorticotropin hormone (ACTH) is a peptide of 39 amino acid residues. Ovine, porcine, and bovine ACTH differ from human ACTH only at the amino acid positions 25,31, and 33. The loss of one amino acid from the N-terminal end of the molecule by hydraulic cleavage results in complete loss of biological activity. In contrast, a number of amino acids may be split off of the C-terminal end with no effect on potency. A 20-amino acid peptide (sequence 1-20) retains the activity of the parent hormone.

In vivo, ACTH stimulates the human adrenocortex to secrete cortisol, corticosterone, aldosterone, and a number of weekly androgenic substances. Absent ACTH, the adrenocortex undergoes atrophy and the rates of secretion of cortisol and corticosterone, which are marketably reduced, do not respond to otherwise-effective stimuli.

ACTH acts to stimulate the synthesis of adrenocorticotropin hormones. ACTH controls its target tissue through the agency of cyclic AMP.

ACTH has been manufactured for commercial use as corticotropin for subcutaneous, intramuscular, or intravenous administration. The preparation is derived from the pituitaries of mammals used for food. The most important use of a ACTH as a diagnostic agent is in adrenal insufficiency. Therapeutic uses of ACTH have included the treatment of adrenocortical insufficiency and other disorders that are responsive to glucocorticoids. Also, ACTH stimulates secretion of mineral corticoids such that it may cause acute retention of salt and water.

Fragments of ACTH have been studied, the studies being most recently described by DeWeid (3).

SUMMARY OF THE INVENTION

In accordance with the present invention, there is provided a method of reducing the rise in intracranial pressure accompanying head trauma by significantly reducing the mean trauma induced increase in blood brain barrier permeability and significantly reducing the peak rise intracranial pressure.

The present invention further provides the use of a compound for treating head trauma induced rises in intracranial pressure which comprises administering an effective amount of an analog of amino acids 4-9 of adrenocorticotropin hormone.

FIGURE IN THE DRAWINGS

Other advantages of the present invention will be readily appreciated as the same becomes better understood by reference to the following detailed description when considered in connection with the accompanying drawings wherein:

FIGS. 1a-c show a head impactor and enlarged plan and elevational views of the head mounting fixture thereof used in developing the mechanical injury model of moderate closed head injury;

Figure 7:
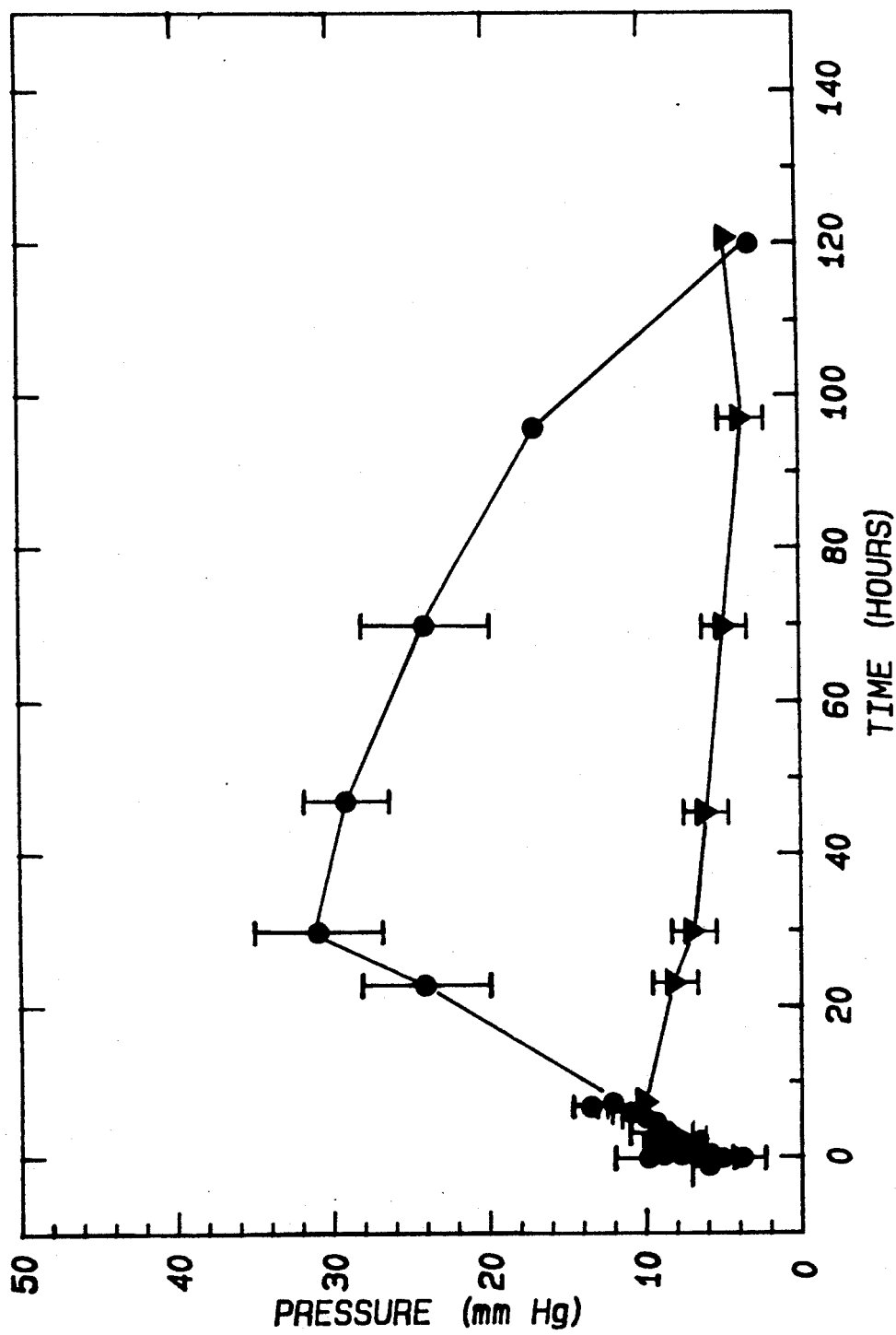
Figure 8:
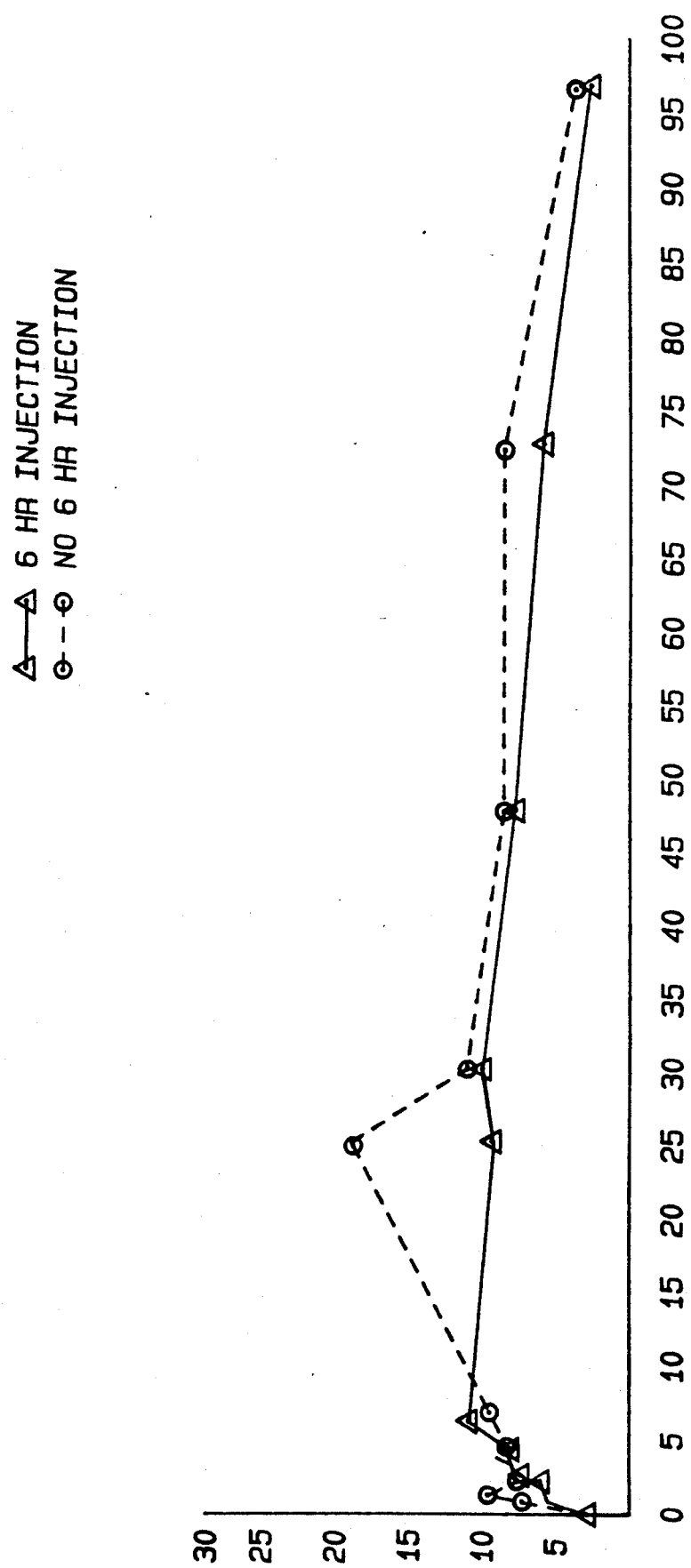

FIG. 7 is a graph showing intracranial pressure after moderate concussion and the effect of Organon 2766, intracranial pressure being measured with a chronic epidural cannula, N=5. Shaded area is control pressure, Organon 2766 being administered subcutaneously at 5 minute 6 hour and 24 hour post concussion; and FIG. 8 is a graph showing intracranial pressure after moderate concussion and the importance of treatment with Organon 2766 at 6 hours post-concussion, intracranial pressure measured with a chronic epidural cannula, N=4, Organon 2766 being administered subcutaneously at 5 minutes and 24 hours post-concussion (⊙- - -⊙) and at 5 minutes 6 hours and 24 post concussion (Δ-Δ).

DETAILED DESCRIPTION OF THE INVENTION

The present invention provides a novel treatment for central nervous system damage caused by moderate concussion. Generally, the method includes the steps of significantly reducing the mean trauma-induced increase in blood brain barrier permeability and significantly reducing the peak rise in intracranial pressure.

More specifically, the syndrome caused by moderate concussion can be divided into two phases as discussed above. As discussed above the first phase is an acute phase consisting of about six hours during which the organism may be lethargic but functional and intracranial pressure is less than 15 mmHG. During the second phase, beginning at six hours and extending up to five days, the organism may become comatose. During the second phase, intracranial pressure increases to more than 20 mmHG at 24 hours and it may approach 40 mmHG. It is this second phase, sometimes called the secondary injury, that it is proven to be intractable to treatment in clinical citings in which very often reduces serious irreversible brain damage. It is also the secondary injury which is effectively treated by the present invention.

The inventive method of treating the rise in intracranial pressure accompanying head trauma is accomplished by administering an amount of an analog of amino acids 4-9 of ACTH effective to significantly reduce the mean trauma-induced increase in blood brain barrier permeability. Applicant has tested many analogs of ACTH 4-10 and has found all to have activity in this regard. Absent the rise in intracranial pressure during the secondary phase of the head trauma, histological studies have shown significant and dramatic reductions in anatomic degradation of the brain tissue. Examples of analog of ACTH peptides 4-10 which have been used in accordance with the present invention are:

1) Met ($O_2$) Glu-His-Phe-D-Lys-Phe. (Peninsula Laboratories Cat #8742). MW:870.07 (also known as Organon 2766). Other Peptides:

2) Bachem product (Cat# PACT 110) Met-0-Glu-His-Phe-D-Lys-Phe. MW:854.1

3) Alpha-MSH MW: 1665 Peninsula Lab. #7251.

The native peptide fragment ACTH$_{4\text{-}10}$, is as follows: Met-Glu-His-Phe-Arg-Try-Gly, MW:962.06. The peptide analogs are modifications of ACTH$_{4\text{-}10}$, the modifications having been made for various purposes. For example, Organon 2766 is a modified peptide made less acceptable to enzymatic degradation resulting in a longer half life in vivo. It has been reported that Organon 31433 and Hoeschst 427 are more potent analogs compared to Organon 2766 (5). However, these last two mentioned analogs are not yet commercially available. Applicants are not aware of chemical trials involving fee compounds.

Subcutaneous injections of nanomolar concentrations of the neuropeptides discussed above have been found to be nontoxic and have prevented the dangerous 24 hour rise in intracranial pressure. Further, it has been found that these nanomoler concentrations administered sub-cutaneously have maintained intracranial pressure near normal levels for up to six days after moderate concussion. This prevention of the swelling of the brain which normally results in structural damage to the brain is directly attributable to the administration of the neuropeptide. This has been confirmed by histological examination of brains of treated rats wherein evidence of damage due to edema or diffuse axonal injury is absent.

Due to the quick onset of the primary and secondary phases off injury following moderate concussion, administration of the neuropeptides is best achieved by routes which provide immediate biovailability of the drug. However, it is expected that the mechanism of action of the present inventive may be useful in the treatment of common other disease states which may not require such immediate bioavailability. Accordingly, the present invention in its broadest application could utilize alternative routes of administration.

Moreover, the use of the analogs in accordance with the present invention are site specific. That is, concomitant with the moderate concussion is an increased permeability or leakiness in areas of the blood brain barrier. The analogs used in accordance with the present invention do not enter where the permeability has not been affected. The analogs only enter the areas where the permeability has been increased. Hence, the analogs used in accordance with the present invention are site specific. This is further applicable to other conditions where increased vascular permeability has occurred. The increase in vascular permeability allows bioavailability of the analog to the area where its effects are needed. Hence, the analogs used in accordance with the present invention can effect vascular permeability by significantly reducing vascular permeability in a site specific manner.

There is evidence to support the clinical application of the present invention. It has been reported that Organon 2766 prevented the neurotoxic side effects cisplatin in rats (6). It has also been recently reported that Organon 2766 attenuated the cisplatin neuropathy without adversely effecting the cytotoxic effect of the drug in women with ovarian cancer in a double-blind, placebo-controlled, randomized trial (8). Two doses were used (0.25 mg/ml and 1.0 mg/ml dissolved in the water) at 1.0 ml/meter$^2$ of body surface area. Placebo consisted of 0.25 mg/ml of mannitol dissolved in water. No toxic effects were noted. The preliminary toxicology studies are contained in an internal report by the same researches (9). Variables examined consisted of threshold value for vibration perception, and a collection of four neurologic signs and seven neurologic systems. The high dose group had significantly fewer signs and symptoms ($p < 0.05$) and a significantly less increase in threshold value for vibration perception ($p < 0.005$). In additional clinical trials, relatively large doses of Organon 2766 in humans were not effective in treating dementias (7,10,11,12) or alcoholic inebriation (13) but were found to be non-toxic and had no serious side effects, in addition to being behaviorally ineffective. Hence, it can be concluded that doses found to be effective in accordance with the present invention are significantly below those doses previously used for treating various diseases in humans and significantly below doses which are already found to be non-toxic and have no serious side effects.

EXPERIMENTAL EVIDENCE

The following experiments demonstrate the effectiveness of the analogs of amino acids 4-9 of ACTH to reduce the central nervous system damage-induced secondary increase in intracranial pressure in a mammalian model of moderate concussion. The following data was generated utilizing the Peninsula Laboratories analog catalog number 8742, having molecular weight of 870.07. This analog is identical to the Organon 2766 analog, as discussed above.

Applicant has developed a reliable physiologic model of potentially reversible, controlled fixed and closed-head injury in the laboratory rat (Wistar, Harlan Sprague-Dawley, Inc. Indianapolis, Ind.) that mimics many of the features of moderate concussion in humans. The model permits long term examination of subsequent cerebrovascular pathophysiological sequelae in conscious, unrestrained animals.

Model Development

Figure 1A:
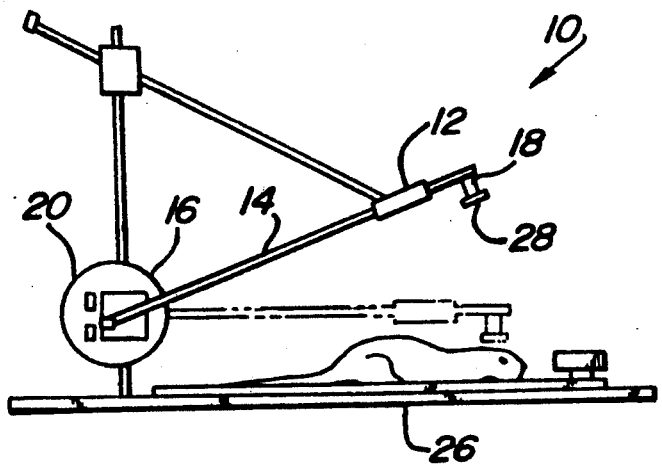

Head Impactor (FIG. 1a)

A pendulum striker 10 was built somewhat after the device used by Bakay (14) to study pathological changes in rat brains including gross alteration of permeability of brain capillaries (4). The weight 12 of the pendulum arm 14 was 911 g, with the center of percussion located near the center of the striking face, 210 mm from the rotational axis 16. A force-measuring transducer 18 (PCB Piezotronics, Depew, N.Y.) was applied to the face of the pendulum. Applied force over time was sampled by means of a storage oscilloscope. Kinetic energy of the device at impact was determined from the potential energy corresponding to the product of pendulum weight and amount of elevation of the center of gravity, measured by the protractor 20 shown in FIG. 1a.

Figure 1B:
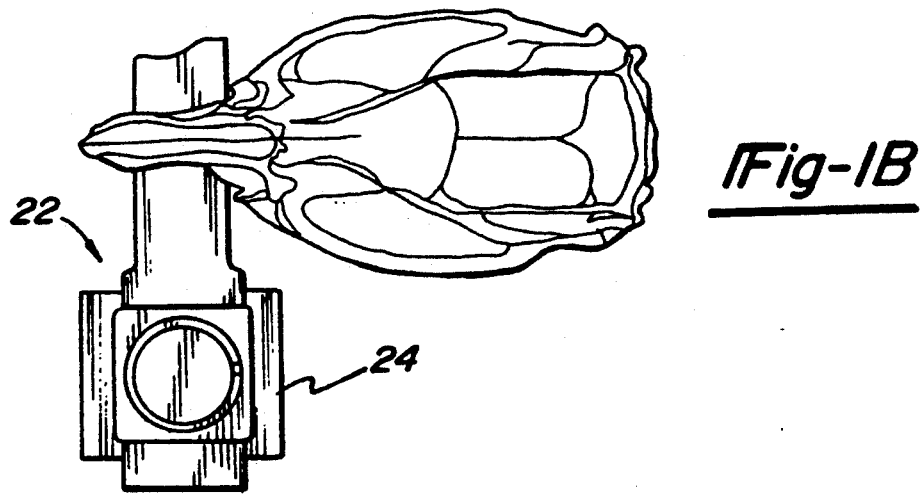

Head Mounting Fixture (FIG. 1b and c)

The fixed-head model which is now utilized allows the pendulum 14 to fall on the midline skull on an anesthetized rat, approximately 9 mm anterior to the coronal suture. In this model, the rat's premaxillary and maxillary bones rest on a wide bite plate located behind clipped lower incisor teeth. The bite plate 22 is attached by means of resilient urethane elastomeric material 24 to a wooden board 26 which also supports the animal's body.

In the following experiments, animals were aligned so that the force of the pendulum 14 was directed with a small encephalo-caudal component 28 which produced predominantly rostral focal injury of the rat forebrain. The striking force was applied to the midline of the skull 9 mm rostral from the bregma. Utilizing this alignment, studies were performed to determine the maximum forces that could be applied which would produce a moderate concussion, i.e. unconsciousness, absence of skull fractures and minimal histopathology, in rats varying in weight from 330 to 430 g. This data was used to devise a nomogram to determine the optimum striking angle in future experiments.

Concussion Procedure

Figure 1C:
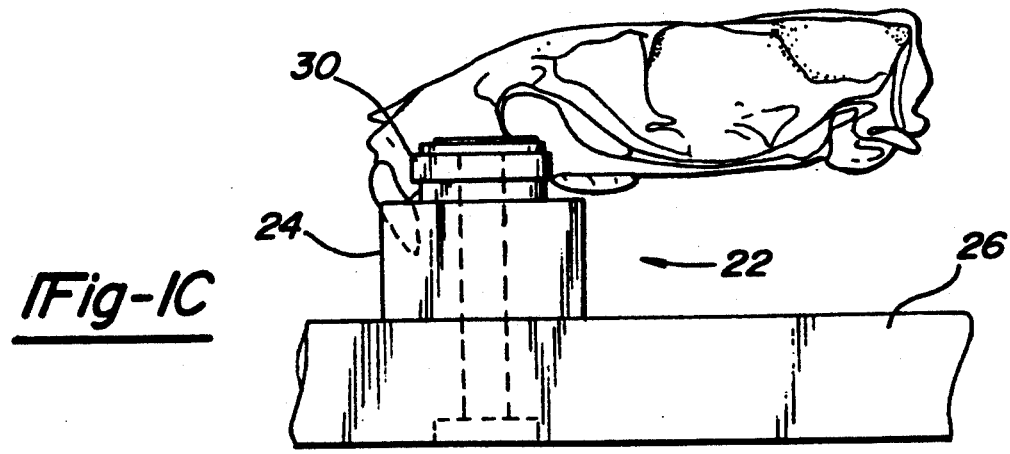
Figure 6:
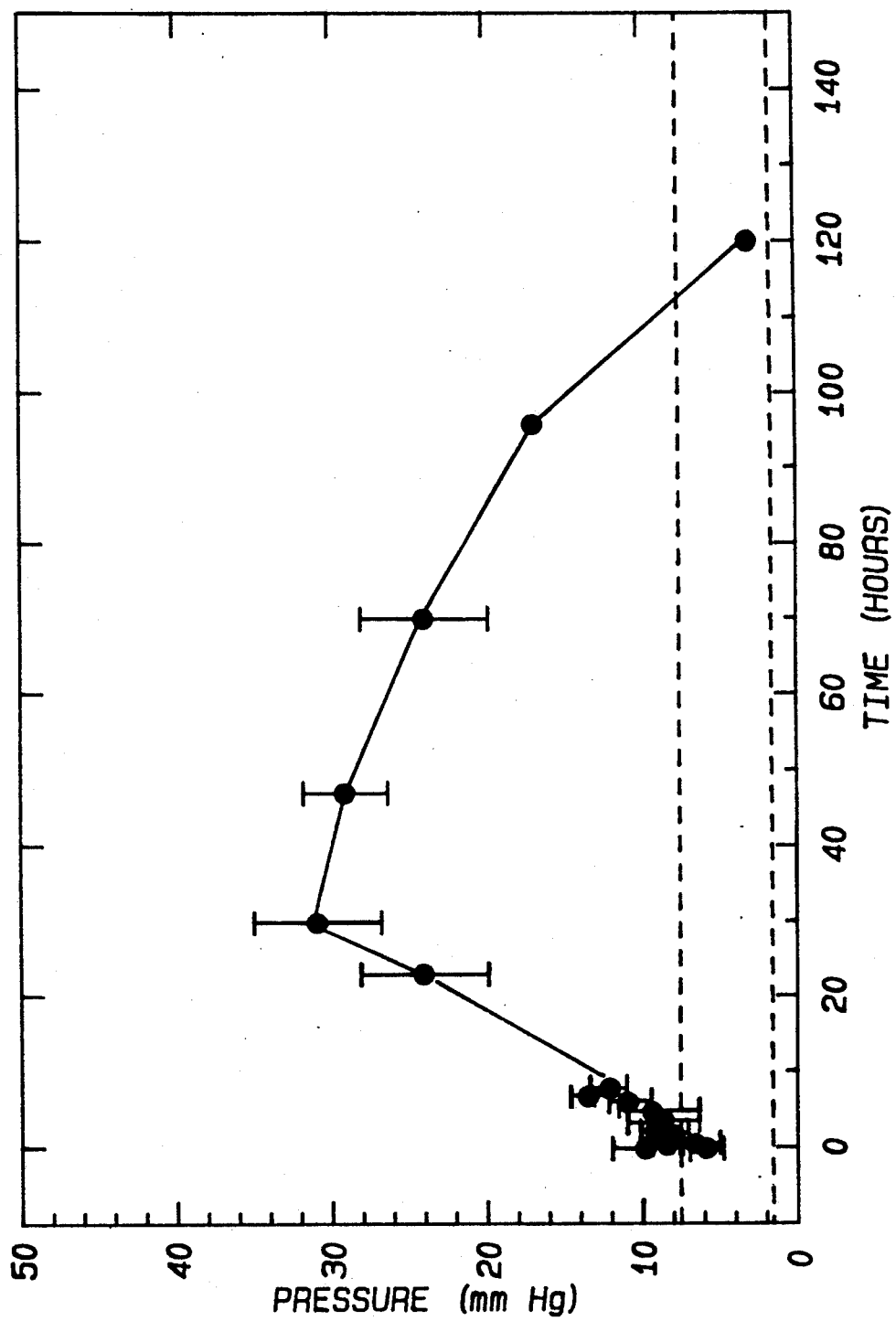
FIG. 6 is a graph showing intracranial pressure changes with time after moderate concussion, intracranial pressure being measured with a chronic epidural cannula, N=5, shaded area being control pressure.

A rat anesthetized with halothane was mounted in a prone position on the test board and the head was fixed in position by means of the bite plate 30 over which the upper incisors were engaged as shown in FIG. 1c. The board angle of recline and the axis of pendulum rotation were adjustable to permit a flat or angled (3°-5°) strike on the chosen head impact site. The optimum applied force/angle was selected from the nomogram. The pendulum was raised to the desired angle and released through a quick-release mechanism to fall into impact with the head. Forces developed by this means ranged from 60 to 85 pounds. The model was tested under the above conditions for its ability to produce changes in regional cerebral permeability (FIG. 3), blood flow (FIG. 4), as well as, intracranial pressure (FIGS. 6, 7 and 8).

Circulation Measures-Permeability

Regional permeability of slowly diffusible substances, such as sucrose, together with the brain intravascular space was estimated by methods of Rapoport (15). The theoretical bases for such measurements have been elegantly described by Blasberg, Patlack and Fernstermacher (16).

Typically a tracer amount of a slowly diffusible indicator is injected intravenously and the arterial plasma concentration is followed until the animal is killed 10 minutes later, time T, so that only a small amount of the tracer has accumulated in the brain. Under these circumstances, brain concentration remains insignificant as compared to plasma concentration, and back-diffusion from brain to plasma can be ignored. Brain uptake of tracer can be given as follows:

$$dC_{brain}/dt = K_t C_{plasma} \qquad [1]$$

where $K_t$ is an "apparent", unidirectional, blood-to-brain transfer constant and $C_{plasma}$ is the indicator concentration in the plasma, its major exchangeable compartment. $K_t$ is employed here as an estimate of permeability and, in the case of sucrose, is considered to be equivalent to the product of the permeability coefficient of sucrose and a constant capillary surface area (rPS).

Integration of equation [1] to time T gives $K_t$ in terms of $C_{brain}$ (T) and the plasma concentration integral $$K_t = \frac{C_{brain}(T)}{\int_o^t C_{plasma}\, dt} \quad [2]$$

$C_{brain}$ in equation [2] represents the parenchymal (extravascular) brain concentration of the poorly diffusible tracer at the time of death, T, and equals net brain concentration minus intravascular content of tracer. The latter term is the product of the whole blood concentration of tracer (at time T) and the regional blood volume.

Cardiac output (CO) can be estimated from a knowledge of the early arterial history of an injected tracer (sucrose this case), which is injected in an intravenous bolus, as follows:

$$CO = \text{Injected dose}/\int_o^t C_{blood}\, dt \quad [3]$$

In equation [3], the integrated arterial concentration of the tracer is corrected for recirculation, as described by Sapirstein (14).

Brain vascular volume (BVS) and permeability were determined simultaneously utilizing modified methods of Rapoport, as described below (18). The BVS was estimated from a knowledge of the $^{14}$C-sucrose content in 16 brain regions relative to that in arterial blood 15 seconds after its injection through an indwelling femoral venous catheter. At this short time interval, brain contents of both $^{14}$C-sucrose and $^{125}$I-albumin, a common intravascular marker, are similar, indicating that virtually all of the sucrose is still in the intravascular compartment. Moreover, estimates of BVS determined with either tracer are in agreement with published values obtained at more conventional time-intervals, e.g., two to ten minutes, after intravenous injection with an error of less than 4%. Thus, the brain content of $^{14}$C-sucrose at 15 seconds provides an acceptable estimate of regional BVS. The procedure outlined below employs $^{14}$C- and $^{3}$H-sucrose markers for the simultaneous measurement of BVS and rPS, respectively.

Permeability Protocol

The experimental protocol for the measurement of blood-to-brain transfer of diffusion-limited substances such as sucrose involved surgical implantation of catheters, one in a femoral vein, the other in the opposite femoral artery, under halothane anesthesia. Following surgery and intravenous injection of Evan's Blue dye (40 mg/kg dissolved in isotonic saline) controlled brain injury was administered immediately after interruption of halothane delivery. The behavior of the animal was carefully monitored. Artificial respiration was not usually required since interruption of breathing rarely accompanied the degree of impaction employed. In the absence of impaction, animals righted themselves within two minutes post-anesthesia. In impacted animals, the period of unconsciousness exhibited after two minutes was attributed to the effect of impact and usually lasted four to ten additional minutes. At this time, animals fully righted themselves in response to a mild tail pinch.

Permeability was measured at two hours after impaction in conscious, catheterized animals which were neither chemically nor physically restrained in the following manner. Arterial blood samples were collected for hematocrit and blood-gas assays. A bolus containing 10–20 μCi of $^{3}$H-sucrose tracer was injected intravenously. This was followed by collection of 17 precisely timed arterial samples (15 μl each) over minute period to determine the integrated plasma content of tracer. At the end of this ten minute period, regional brain intravascular spaces (BVS) were measured by means of a second intravenous bolus injection 4 μCi of $^{14}$C-sucrose. Arterial blood was sampled every second for an additional 20 seconds, at which time the animal was killed with a rapid intravenous injection of saturated potassium chloride. Thus, permeability and BVS were determined simultaneously by means of the application of a combination of Rapoport's methods (15, 18).

Additionally, it was possible to derive an estimate of the cardiac output from the arterial washout curve of either of the tracers after corrections were made for recirculation 14. Brains were removed immediately after death and 16 regions were dissected on a chilled steel plate. The regions of interest included the pons-medulla, cerebellum, hypothalamus, basal ganglia, septal area, midbrain, inferior colliculus, superior colliculus, dorsal hippocampus, pyriform cortex-amygdala, frontal cortex, parietal cortex, occipital cortex, white matter, olfactory bulb ad olfactory tubercle. Tissue and blood contents of this tracer were readily extracted in Bray's scintillation cocktail without further treatment (>98%) and counted in a quench-correcting multichannel scintillation spectrometer (Packard 4530). All cerebrovascular measurements were performed between 0900 and 1300 hour.

Circulation Measures-Blood flow method

Blood flow was measured by an updated version of applicants method (19) which employs the fractionation of a bolus of $^{14}$C-iodoantipyrine and includes a correction for the time-dependent afflux of the tracer from brain tissues. The method also incorporates a "dye"-dilution technique for the simultaneous measurement of the cardiac output in which the isotope replaces conventional dyes (17).

The indicator bolus fractionation technique for the measurement of blood flow can be substituted for the more complex Kety-Sokoloff procedure (20) under certain circumstances. It has been shown that the Kety equation and the bolus fractionation equation are similar when the killing time is short and the tissue reservoir for the indicator is large in relation to inflow (16). Under these conditions a tissue's uptake of the indicator and its blood flow are related as follows:

$$U_i I \approx F_i I CO \quad [4]$$

where $U_i$ is the tissue content of indicator, I is the body uptake of indicator (equivalent to the injected dose of indicator in these experiments), and CO is the cardiac output (Equation [3]). Equation [4] states, that when a highly diffusible indicator, such as iodoantipyrine, is administered in a single intravenous injection and the killing time is short, then the pattern of iodoantipyrine distribution in the brain is the same as the pattern of the fractional distribution of the cardiac output. Since a single intravenous injection is substituted for the complex continuous infusion in the Kety method and since this can be accomplished under essentially non-traumatic circumstances, the single-injection technique makes possible more responsive blood flow values in conscious, unrestrained animals.

Blood flow protocol

Animals were catheterized in one femoral vein and opposite femoral artery under controlled halothane anesthesia and Evan's Blue dye was injected as described in the permeability protocol above. Two hours after impaction, arterial blood was sampled for hematocrit, pH, $PaCO_2$ and $PaO_2$. A single bolus containing isotonic saline and 4 $\mu$Ci $^{14}$C-iodoantipyrine was injected intravenously. Arterial blood was sampled at 15 $\mu$l/sec for 15 seconds to establish the arterial concentration curve for the indicator. At 15 seconds, animals were killed with an intravenous injection of a bolus of saturated potassium chloride solution (250 $\mu$l). Brains were quickly removed and rapidly dissected on a chilled steel plate. Brain regions were weighed electronically and prepared for counting as described above.

Intracranial pressure (ICP) measurements

Intracranial pressures were determined in separate but identically treated animals. A 1 mm hole was drilled into the interparietal plate of the rat skull at a point 2 mm from the midline and 2 mm caudal to the suture. A stainless steal cannula constructed from a 23 gauge needle with an 8 cm extension of PE50 polyethylene tubing filled with isotonic saline was inserted epidurally into the craniotomy. A stainless steel screw was placed opposite to the cannula. Dental acrylic cement sealed the cannula and anchor screw in place. A Camino 431 miniature pressure sensor was inserted into the tubing and pressure was measured on Camino 420 Digital Pressure Monitor System. Intracranial pressure measurements were monitored from 5 minutes before and up to 120 hours following head impaction.

Histology

Animals were deeply anesthetized with sodium pentobarbital (50-60 mg/kg,ip) and sacrificed by transcardiac perfusion with 100 ml of physiological saline containing 0.5% procaine hydrochloride followed by 150-250 ml of 10% phosphate-buffered formalin. Just prior to perfusion, each animal received 500 units of heparin directly into the left ventricle. Following perfusion, brain were removed and hardened in additional volumes of fixative for a period of 7-20 days. The entire brain was sectioned in the frontal plane on a freezing microtome at 30 micrometers and processed for degenerating neurons and axons. A sensitive selective silver impregnation procedure, the Fink-Heimer technique, was used to visualize degenerating axons of all calibers, both myelinated and unmyelinated. Alternate sections were stained for neuronal degeneration utilizing the Nissl stain, thioneine.

Drug Administration

Initial preparation

The peptide (5 mg vial from manufacturer) was diluted with 5 ml of distilled water, pipetted into polypropylene tubes (150 ug/tube), placed in a Savant centrifuge and lyophilized under pressure for 1.0-1.5 hours. Tubes were removed from the centrifuge, capped and stored at +4 degrees centigrade under vacuum pressure. The pressure was reestablished every 2-3 days.

Administration

On the day of administration, the tube was removed from the refrigerator, placed on ice, and dissolved in 1.1 ml of sterile bacteriostatic saline (benzyl alcohol added). At the time of the injection, either 0.1 or 0.2 ml of the solution was drawn into a 1 ml disposable tuberculin syringe, with a 25 gauge needle attached. Injection was subcutaneous in the dorsal neck area of the animal.

Dose schedules, toxicity, efficacy

Figure 2A:
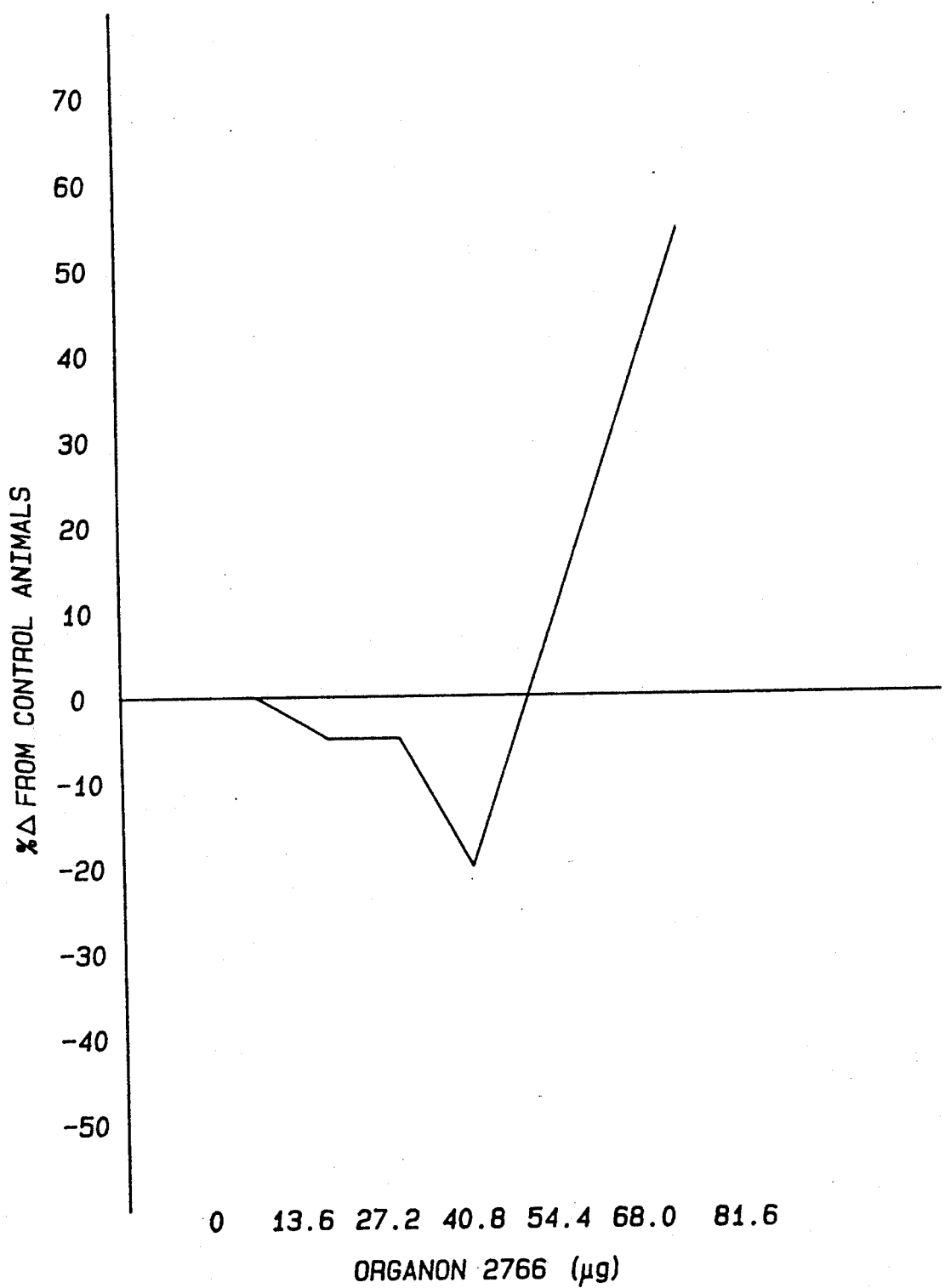
FIG. 2A is a dose response curve for Organon 2766 showing the effect on blood-brain barrier permeability (mean of 16 tissues) in control animals 2 hours after anesthesia.
Figure 2B:
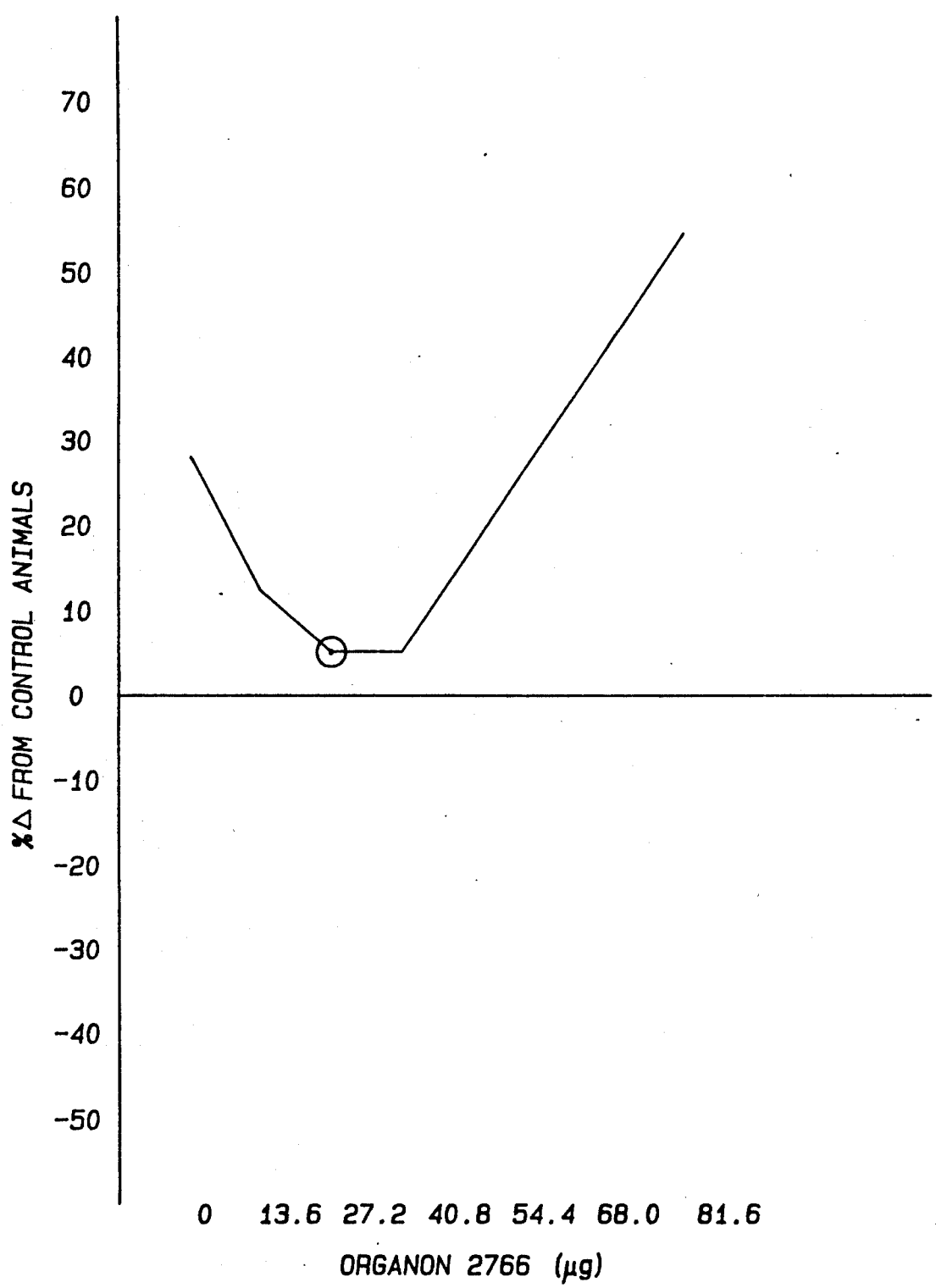
FIG. 2B is a dose response curve showing the effect on blood-brain barrier permeability (mean of 16 tissues) in animals subjected to head trauma 2 hours earlier.

Animals in the two hour permeability and blood flow experiments were injected at either five minutes or 30 minutes post impact with either 13.6 ug (0.1 ml of the solution) or 27.2 ug (0.2 ml of the solution). Both times were equally effective. The latter dose was slightly more effective using permeability as the experimental variable, and was chosen as the dose for the subsequent blood flow and the intracranial pressure experiments as demonstrated by the dose response curve, FIG. 2. In the animal population used, the 27.2 $\mu$g dose=65-75 ug/kg. Doses up to four times this amount are not lethal, however at this high dose, permeability of the blood-brain barrier is dramatically increased in both control animals and in impacted animals. Hence, this dose was interpreted as detrimental, if not toxic, in impacted animals. This inverted bell-shaped curve has been noted elsewhere for this peptide analog (5).

In the intracranial pressure experiments, animals were injected at 5 minutes, 6 hours and 24 hours post trauma. The 6 hours injection appears to be critical since animals receiving only the 5 minute injection had elevated ICP's at 24 hours which subsequently decreased following the 24 hour injection (See FIG. 8)

Results from Animal Experiments

Permeability

Figure 3:
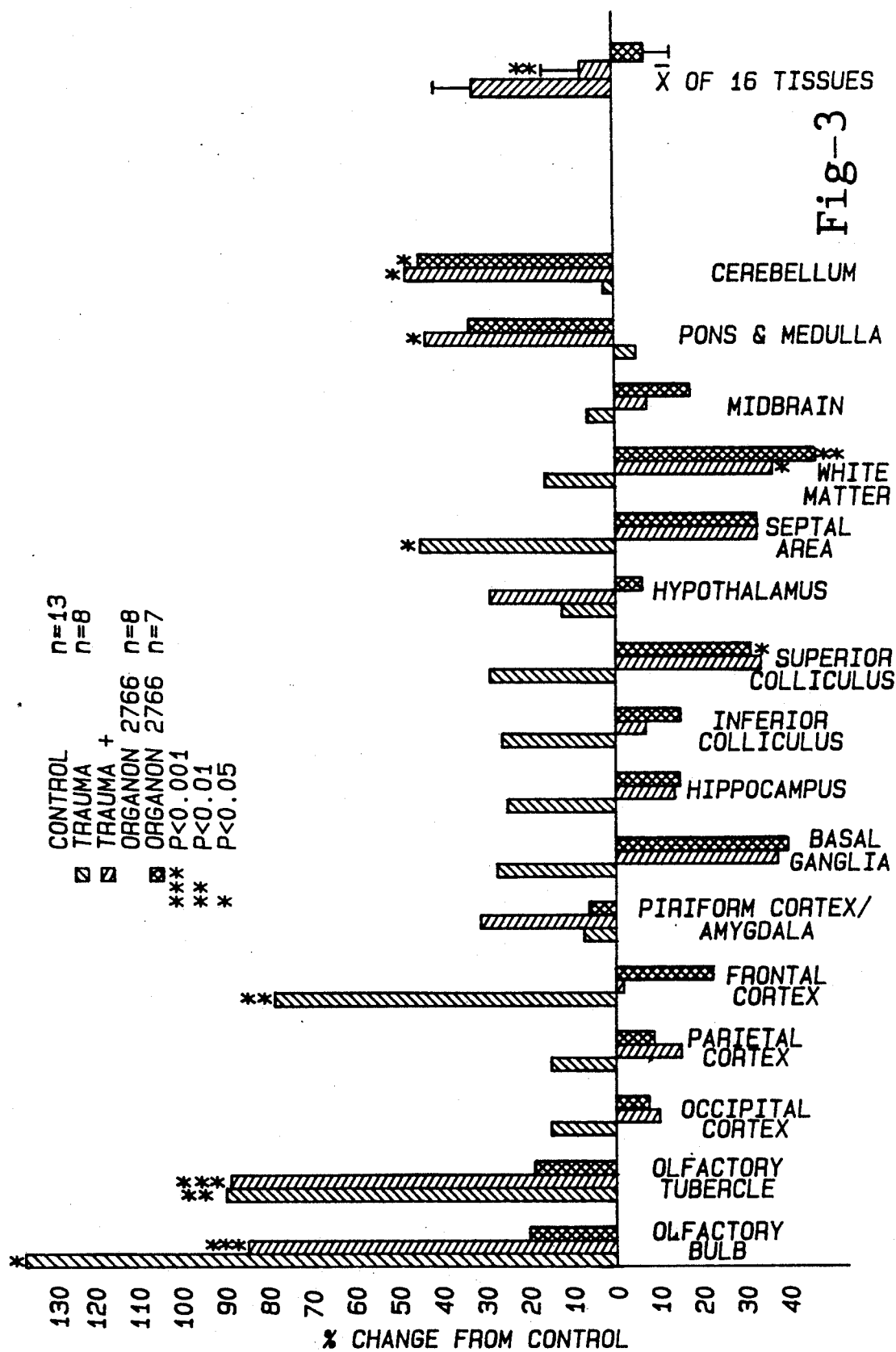
FIG. 3 is a graph showing the effect of trauma and Organon 2766 on regional cerebrovascular permeability 2 hours after insult, permeability-capillary surface are products (rPS) of $^3$H-sucrose tracer based on 10 minute regional uptake and expressed as ml/g/sec $\times 10^6$, mean ±SEM, significance being determined by Student's t-test.

The 27.2 ug dose of the peptide reduced the mean trauma-induced increase in blood brain barrier (BBG) permeability at 2 hours from 32% to 8.7% (FIG. 3). This decrease was statistically significant (p <0.01.) In the tissues (7) in which BBB increased in impacted animals which received the peptide compared to non-impacted, saline controls, it also increased in control non-impacted animals receiving the analog. In two of these tissues (significantly affected by the impact), the increases were less than those produced by trauma alone. The hind brain appears to be particularly sensitive to the peptide.

Cerebral Blood Flow

Figure 4:
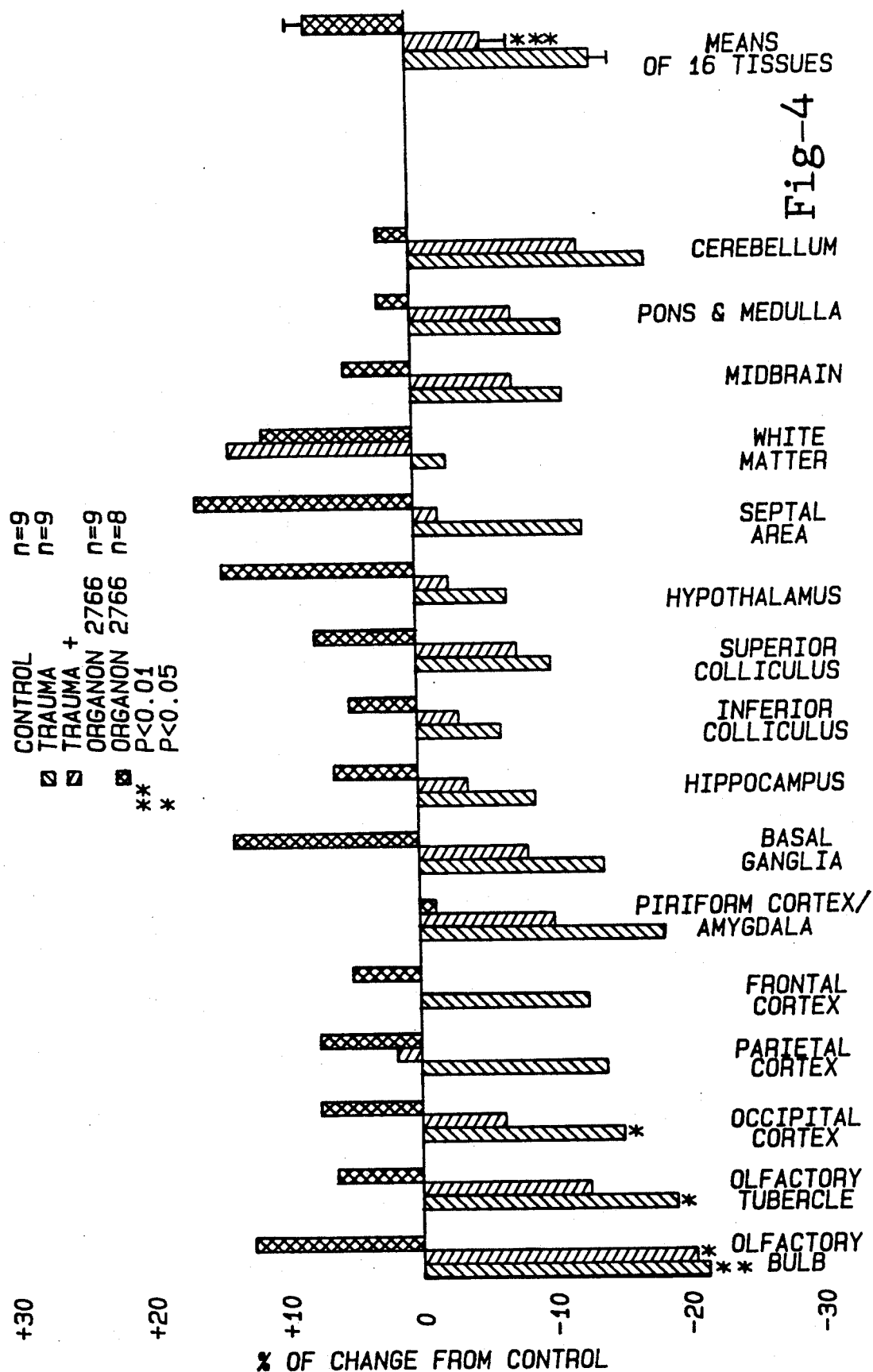
FIG. 4 is a bar graph showing the effect of closed-head trauma and Organon 2766 on regional cerebral flow 2 hours after insult, regional cerebral blood flow based on 15 second uptake of $^{14}$C-iodoantipyrine tracer and is expressed as ml/g/min, mean ±SEM, significance being determined by Student's t-test.

Head trauma reduced cerebral blood flow by an average of 12.4% (FIG. 4). Administration of the peptide to impacted rats increased blood flow to a mean reduction of 5.4% compared to control non-impacted animals (P <0.001). In control, non-impacted rats, the peptide analog increased cerebral blood flow by 7.3%. This pattern was observed in all but 3 tissues. In the parietal and frontal cortical tissues and callosal white matter, blood flow was either increased or returned to control values in impacted animals as a result of the administration of the peptide.

Blood Gases and Cardiovascular Parameters

Figure 5:
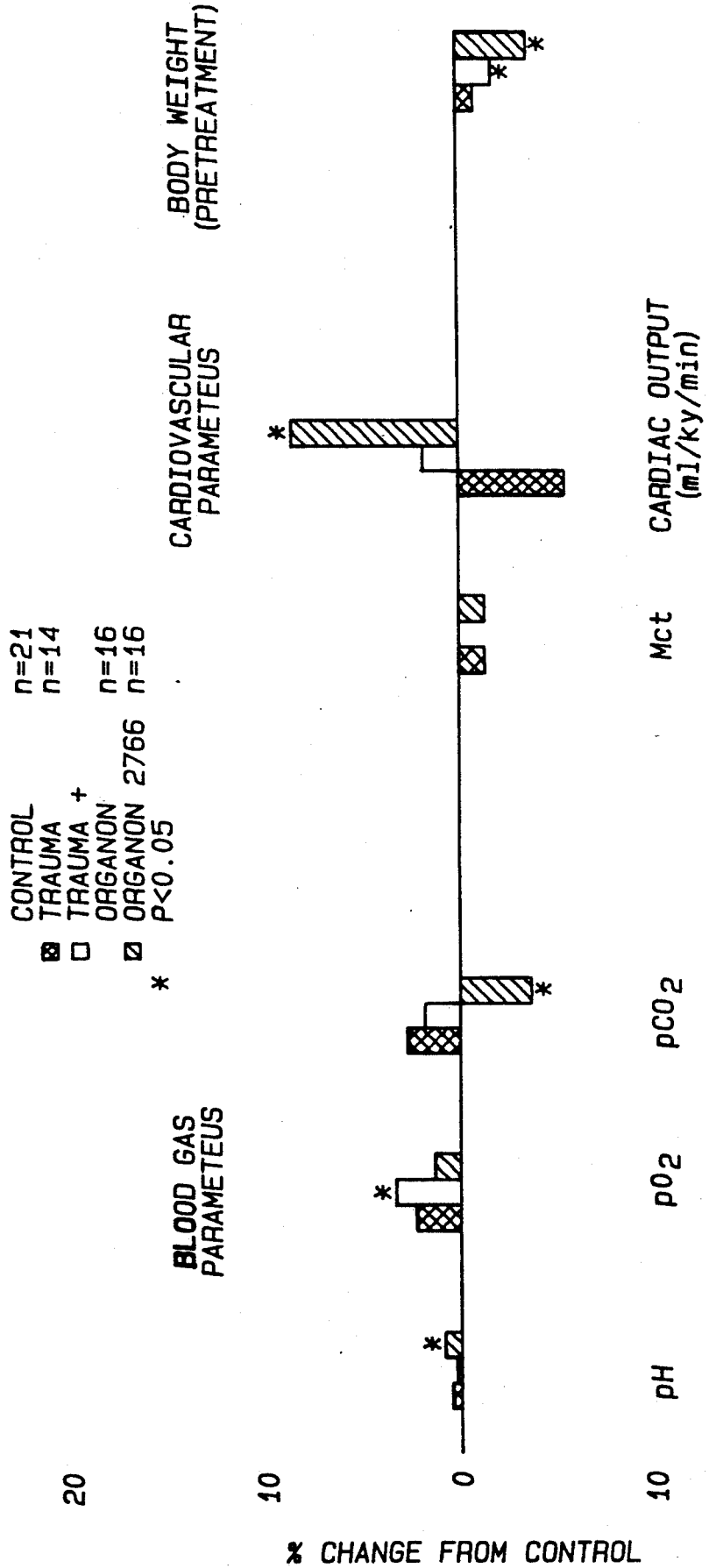
FIG. 5 is a graph showing the effect of closed-head trauma and Organon 2766 on arterial blood-gas and cardiovascular parameters 2 hours after insult.

Head trauma in the model did not significantly affect blood gases or pH at two hours; however both pO2 and pCO2 were elevated compared to control animals (FIG. 5). Administration of the peptide to impacted rats raised $pO_2$ significantly by 5%; $pCO_2$ was increased, but not significantly compared to saline control non-impacted animals. In control animals receiving the peptide, $pO_2$ was increased and $pCO_2$ was significantly decreased by 6% (p <0.05). pH was unchanged in impacted animals receiving the peptide but significantly increased (1%) in non-impacted animals receiving the peptide.

Hematocrit was not significantly affected in any of the groups compared to control animals (FIG. 5). However, head trauma caused a non-significant decrease in cardiac output which was restored by administration of the peptide. Moreover, the peptide increased cardiac output in control animals by 13% which may account for some of the changes seen in cerebral blood flow in animals receiving the peptide.

Intracranial Pressure

In the model of moderate concussion post-injury, time-dependent ICP changes occurred in roughly two phases: a rapid increase to about mmHg during the first 6 hour period followed by a steady increase which peaked by 30 hours with an average pressure to 30 mmHg (FIGS. 6 and 7). Although ICP decreased slowly thereafter, relatively high levels (>20 mmHg) were still observed up to 72 hours post injury. Average ICP fell below 20 mmHg only after 96 hours post injury. In stark contrast, animals receiving the peptide analog at 5 minutes, 6 hours and 24 hours post-injury suffered no secondary rise in ICP after 6 hours (FIG. 6). While the peptide did not affect the early rapid rise to about 10 mmHG at 6 hours, mean ICP levels in drug treated animals which had received a moderate concussion remained below 10 mmHg for up to 6 days. Uninjured animals receiving the peptide at the same time periods and dose levels were not different from control animals.

Statistics

Cerebral permeability and blood flow measures in head-injured and uninjured control animals were compared by means of Students t test. A level of probability of $P<0.05$ was considered statistically significant.

All experiments have been reviewed by the Wayne State University Animal Care Committee and have met, or exceeded AAALAC and DHEW standards as defined in the *Guide for Care and Use of Laboratory Animals (DHEW Publication No. (NIH)* 78-23.) All surgical and injury procedures were carried out under anesthesia; 1.5% halothane (induction), 0.5-1% maintenance.

The above experiments demonstrate the effectiveness of the present invention as a method for reducing the rise in intracranial pressure accompanying head trauma. Further demonstrated is the ability of the present invention to significantly reduce the reduction of cerebral blood flow accompanying the head trauma. Hence, the present invention provides a unique and significant means for the treatment of the effects of at least moderate head trauma as well as other conditions wherein vascular permeability is effected.

REFERENCES

1) E. R. WOLPOW, Harvard Health Letter, volume 16, number 6, April 1991.
2) MILLER, S. D. (1985). Head injury and brain ischaemia—implications for therapy. Brit. J. Anesth. 57:120-129
3) De Weid, D. (Ed.) *Neurooeotides: Basics and Perspectives*, Chap. 1 Effects of peptide hormones on behavior, pp 1–44, Amsterdam, Elsinier, 1990.
4) HALL, E. D. AND BRAUGHLER, J. (1989). Central nervous system trauma and stroke. II. Physiological and pharmacological evidence for involvement of oxygen radical and lipid peroxidation. Free Radical biology & Medicine 6:303-313.
5) WOLTERINK, G., van REE, J. M., van NISPEN, J. W. and deWIED, D. (1991). Structural modifications of ACTH(4-9) analog ORG 2766 yields peptides with high biological activity. Life Sci. 48:155-161.
6) DeKONING, P., NEIJT, J. P., JENNEKENS, F. G. I., AND GISPEN, W. H. (1987). ORG 2766 protects from cisplatin-induced neurotoxicity in rats. Exper. Neurol. 97:746-750
7) FREDERIKSEN, S. O., D'ELIA, G. AND BENGTSSON, B. O. (1985). ACTH4-9 analog (ORG 2766) in depressed elderly patients. I. Effect on depressed mood. Acta Psychiatric Scandinavica 72:341-348.
8) VAN DER HOOP, R. G. VECHT, C. J., VAN DER BURG, M. E., ELDERSON, A., BOOGERD, W. HEIMANS, J. J., VAN HOUWELINGEN, J. C., JENNEKENS, F. G. AND GISPEN, W. H. (1990) Prevention of cisplatin neurotoxicity with an ACTH (4-9) analog in patients with ovarian cancer. N. Eng. J. Med. 322:89-94.
9) Pinder, R. M. Chemical, physical and toxilogical data on ORG 2766. Internal Report. OSS, The Netherlands: Organon International BV, 1986: 1-12.
10) SOININEN, H., KOSKINEN, T., HELKALA, E. L., PIGACHE, R. and RIEKKINEN, P. J. (1985). Treatment of Alzheimer's disease with a synthetic ACTH 4-9 analog. Neurology 35:1348-1351.
11) PARTANEN, J. V., SOININEN, H. and RIEK-KINEN, P. J. (1986). Does an ACTH derivative (ORG 2766) prevent deterioration of EEG in Alzheimer's disease? Electroencephalography & Clinical Neurophysiology 63:547-551.
12) KRAGH-S:RESENEN P., OLSEN, R. B., LUND, S., VAN RIEZEN, H. AND STEFFENSEN, K. (1986). Neuropeptides: ACTH-peptides in dementia. Progress in neuro-psychopharmacology & bilogical psychiatry. 10 479-492.
13) LINNOILA, M., MATTILA, M. J., KARHUNEN, P., NUOTTO, E. AND SEPPALA, T. (1981). Failure of TRH and Org 2766 hexapeptide to counteract alcoholic inebriation in man. European J. Clin Pharmacol. 21:27-32.
14) Bakay, L. et al. Experimental cerebral concussion *J. Neurosurg.* 47:525-531, 1977.
15) RAPOPORT, S. I., FREDERICKS, W., OHNO, K., and PETTIGREW, K. D. (1980). Quantitative aspects of reversible osmotic opening of the blood-brain barrier. Amer. J. Physiol. 38:R421-R431.
16) BLASBERG, R. G., PATLAK, C. S., and FENSTERMACHER, J. D. (1983). Selection of experimental conditions for the accurate determination of blood-brain transfer constants from single-time experiments. A theoretical analysis J. Cereb. Blood Flow Metabol. 3:215-225; also pp 1-32.

17) SAPIRSTEIN, L. A. (1958). Regional blood flow by fractional distribution of indicators. Amer. J. Physiol. 193: 161-168.

18) OHNO, K., FREDERICKS, W., and RAPOPORT, S. I. (1979). Osmotic opening of the blood-brain barrier to methotrexate in the rat. Surg. Neurol 12: 323-328.

19) GOLDMAN, H., and SAPIRSTEIN, L. A. (1973). Brain blood flow in the conscious and anesthetized rat. Am. J. Physio. 224: 122-126.

20) SAKURADA, O., KENNEDY, C., JEHLE, J., BROWN, J. D., CARBIN, G. W. and SOKOLOFF L. (1978) Measurement of local cerebral blood flow with iodo[$_{14}$C]antipyrine. Amer J. Physiol. 234: H59-H66.

What is claimed:

1. A method of reducing the rise in intracranial pressure a mammal accompanying head trauma by systemically administering to said mammal an effective amount of an analog of amino acids 4-9 of adrenocorticotropin hormone (ACTH) selected from the group consisting of:
Met-O$_2$-Glu-His-Phe-D-Lys-Phe-O—(Ch$_2$)$_9$—CH$_3$;
Met-O$_2$-Glu-His-Phe-D-Lys-Phe-NH—(CH$_2$)$_8$—NH$_2$;
Met-O-Glu-His-Phe-D-Lys-Phe;
Alpha-MSH; and
Met-(O$_2$) Glu-His-Phe-D-Lys-Phe.

2. A method as set forth in claim 1 wherein said administering step is further defined as subcutaneously injecting the analog.

3. A method as set forth in claim 2 wherein said administrating step is further defined as administering an ACTH analog modified to render the analog less susceptible to enzyme degradation.

4. A method of treating the rise in intracranial pressure a mammal accompanying head trauma by systemically administering to said mammal an amount of an analog of amino acids 4-9 of ACTH selected from the group consisting of:
Met-O$_2$-Glu-his-Phe-D-Lys-Phe-O—(CH$_2$)$_9$—CH$_3$;
Met-O$_2$-Glu-His-Phe-D-Lys-Phe-NH—(CH$_2$)$_8$—NH$_2$;
Met-O-Glu-His-Phe-D-Lys-Phe;
Alpha-MSH; and
Met-(O$_2$) Glu-His-Phe-D-Lys-Phe.

5. A method as set forth in claim 4 wherein said administering step is further defined as administering an amount of the analog capable of significantly reducing the reduction of cerebral blood flow accompanying the head trauma.

6. A method as set forth in claim 5 wherein said administering step is further defined as subcutaneously injecting the analog.

7. A method as set forth in claim 6 wherein said administering step is further defined as administering an ACTH analog modified to render the analog less susceptible to enzyme degradation.

8. A method of effecting vascular permeability by in a mammal by administering to said mammal an effective amount of an analog of amino acids 4-9 of ATCH selected from the group consisting of
Met-O$_2$-Glu-His-Phe-D-Lys-Phe-O—(CH$_2$)$_9$—CH$_3$;
Met-O$_2$-Glu-His-Phe-D-Lys-Phe-NH—(CH$_2$)$_8$—NH$_2$;
Met-O-Glu-His-Phe-D-Lys-Phe;
Alpha-MSH; and
Met-(O$_2$) Glu-His-Phe-D-Lys-Phe.
and significantly reducing vascular permeability.

9. A method of reducing the rise in intracranial pressure a mammal accompanying head trauma by systemically administering to said mammal an effective amount of an analog of amino acids 4-9 of adrenocorticotropin hormone (ACTH).

* * * * *